(12) United States Patent
Brown et al.

(10) Patent No.: US 8,221,672 B2
(45) Date of Patent: *Jul. 17, 2012

(54) METHOD AND APPARATUS FOR FORMING A BATT OF PARTICULATE MATERIAL FOR USE AS A COMPONENT IN AN ABSORBENT CORE ASSEMBLY

(75) Inventors: Darrell Ian Brown, Mason, OH (US); Bradley Edward Walsh, Cincinnati, OH (US); Joseph Allen Eckstein, Sunman, IN (US); Horst Blessing, Cincinnati, OH (US); Volker Maier, Euskirchen (DE); Siegfried Link, Schleiden (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/023,637

(22) Filed: Feb. 9, 2011

(65) Prior Publication Data
US 2011/0203715 A1 Aug. 25, 2011

Related U.S. Application Data

(63) Continuation of application No. 12/542,789, filed on Aug. 18, 2009, now Pat. No. 7,906,065.

(51) Int. Cl.
*B27N 3/04* (2006.01)
*A61F 13/15* (2006.01)
(52) U.S. Cl. ....... 264/511; 264/517; 264/112; 425/80.1; 156/62.2; 156/62.8
(58) Field of Classification Search .................. None
See application file for complete search history.

(56) References Cited

U.S. PATENT DOCUMENTS

| | | | |
|---|---|---|---|
| 3,882,216 | A | 5/1975 | Delanty et al. |
| 4,761,258 | A | 8/1988 | Enloe |
| 4,940,464 | A | 7/1990 | Van Gompel et al. |
| 4,994,053 | A | 2/1991 | Lang |
| 5,092,861 | A | 3/1992 | Nomura et al. |
| 5,246,433 | A | 9/1993 | Hasse et al. |

(Continued)

FOREIGN PATENT DOCUMENTS
CA 2 051 149 2/2002
(Continued)

OTHER PUBLICATIONS

International Search Report & Written Opinion PCT/IB2006052734, mailed Jan. 23, 2007, 11 pages.

*Primary Examiner* — Mary F Theisen
(74) *Attorney, Agent, or Firm* — Amy M. Foust; Abbey A. Lopez

(57) ABSTRACT

A method and apparatus for forming a batt of particulate material which may be used in an absorbent article. The apparatus may include a vacuum zone, an air impermeable fence zone adjacent to the vacuum zone, and an air permeable fence zone adjacent to the vacuum zone. The air permeable fence zone may comprise an ambient air entry conduit in communication with an ambient air exit port. The method may include providing a laydown drum and a first web of material, positioning the first web of material substantially adjacent to the laydown drum, generating a vacuum through the laydown drum, depositing particulate matter onto the first web of material, and rotating the laydown drum.

20 Claims, 12 Drawing Sheets

U.S. PATENT DOCUMENTS

| | | |
|---|---|---|
| 5,494,622 A | 2/1996 | Heath et al. |
| 5,569,234 A | 10/1996 | Buell et al. |
| 5,897,545 A | 4/1999 | Kline et al. |
| 5,957,908 A | 9/1999 | Kline et al. |
| 6,120,487 A | 9/2000 | Ashton |
| 6,120,489 A | 9/2000 | Johnson et al. |
| 6,706,129 B2 | 3/2004 | Ando et al. |
| 7,297,307 B2 | 11/2007 | Yasumura et al. |
| 7,524,449 B2 | 4/2009 | Walsh et al. |
| 7,906,065 B1 * | 3/2011 | Brown et al. .................. 264/511 |
| 2002/0056516 A1 | 5/2002 | Ochi |
| 2002/0156441 A1 | 10/2002 | Sawyer et al. |
| 2002/0188266 A1 | 12/2002 | Kling et al. |
| 2003/0132556 A1 | 7/2003 | Venturino et al. |
| 2003/0139721 A1 | 7/2003 | Melius et al. |
| 2003/0171728 A1 | 9/2003 | Heyn et al. |
| 2003/0233082 A1 | 12/2003 | Kline et al. |
| 2006/0048880 A1 | 3/2006 | Blessing et al. |

FOREIGN PATENT DOCUMENTS

| | | |
|---|---|---|
| EP | 0 292 623 A1 | 11/1988 |
| EP | 0 478 182 A1 | 1/1995 |
| EP | 0 958 801 B1 | 11/1999 |
| EP | 1 621 167 A2 | 2/2006 |
| FR | 2 521 003 B1 | 5/1987 |
| WO | WO 02/49565 A2 | 6/2002 |
| WO | WO 03/059229 A1 | 7/2003 |
| WO | WO 03/059232 A2 | 7/2003 |
| WO | WO 03/059233 A2 | 7/2003 |
| WO | WO 2008/117109 A1 | 10/2008 |

* cited by examiner

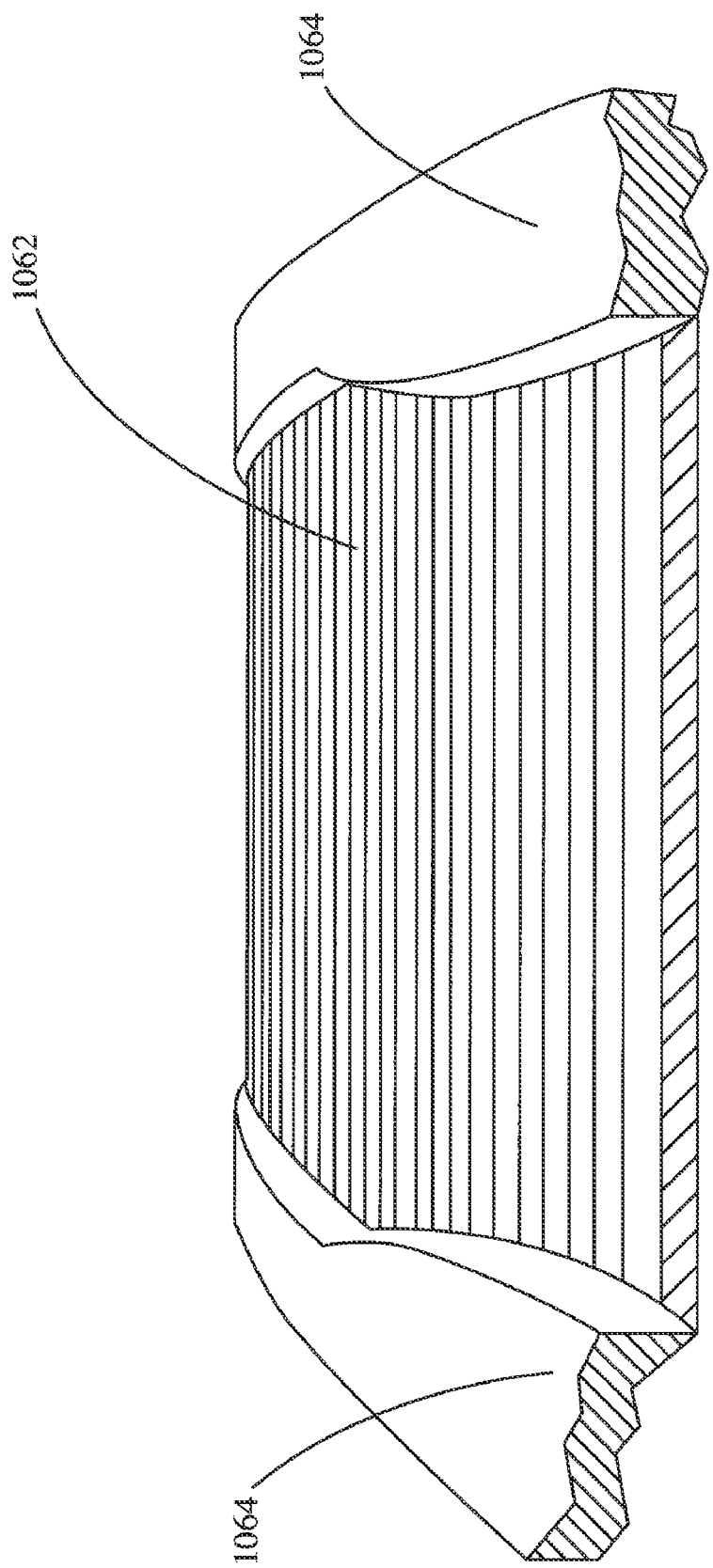

METHOD AND APPARATUS FOR FORMING A BATT OF PARTICULATE MATERIAL FOR USE AS A COMPONENT IN AN ABSORBENT CORE ASSEMBLY

CROSS REFERENCE TO RELATED APPLICATION

This application is a continuation of U.S. patent application Ser. No. 12/542,789, filed Aug. 18, 2009, now U.S. Pat. No. 7,906,065, which is hereby incorporated by reference.

FIELD OF THE INVENTION

The present disclosure relates to methods and apparatuses for manufacturing disposable absorbent articles, and more particularly, methods and apparatuses for forming batts of superabsorbent polymer for use as components in absorbent core assemblies.

BACKGROUND OF THE INVENTION

Disposable absorbent articles, such as diapers, are often constructed with an absorbent core assembly adapted to absorb bodily exudates and positioned between layers of materials. Such absorbent core assemblies may include a mixture of fibrous and particulate materials (e.g., fluff material and superabsorbent polymer), which are formed into a batt or wad. In turn, the batt or wad may be positioned between two or more layers of materials. One such layer may be a dusting layer adapted to face the wearer's body. Another such layer may be a core wrap adapted to face away from the person's body. The batt may not extend the entire length of the diaper, and thus, is generally intended to extend longitudinally inboard of the end edges of the diaper.

In the manufacturing of the absorbent core assemblies, a variety of batt forming techniques may be utilized. For example, discrete batts may be formed with the use of vacuum zones within a laydown drum. In some configurations, superabsorbent polymer and fluff material are deposited onto a web partially wrapped around the outer surface of the laydown drum. Vacuum zones on the outer surface of the laydown drum help place and hold the superabsorbent polymer and fluff material in desired locations on the web. However, using some current techniques and apparatuses, some superabsorbent polymer and fluff material may be inadvertently deposited outside of the vacuum zones and outside desired locations on the web. For example, in some instances, superabsorbent polymer may be deposited substantially along the entire length of the diaper. As a result, the superabsorbent polymer may subsequently migrate through the topsheet, causing the superabsorbent polymer to be deposited on the wearer's skin. Such deposits may cause skin irritation; may be believed to cause skin irritation; and/or may be aesthetically unacceptable to a consumer. Additionally, fluff material inadvertently deposited substantially along the entire length of the diaper may interfere with an end seal necessary to contain the absorbent core assembly.

In response to the aforementioned problems, some laydown drums may be configured with additional systems to help prevent the superabsorbent polymer and fluff mate from migrating outside the vacuum zones. For example, some laydown drums may include pneumatic systems that force compressed air through zones in the laydown drum to help prevent the deposit of particulate material along the entire length of the diaper. However, such systems add cost and complexity to the manufacturing process.

Thus, there remains a need for simplified methods and apparatuses for forming batts comprising particulate material (e.g., fluff material and superabsorbent polymer) for use as a component in an absorbent core assembly.

SUMMARY OF THE INVENTION

In some embodiments, the present disclosure is directed to an apparatus for forming a batt comprising particulate material, the apparatus comprising a support structure having an outer surface, a plurality of vacuum zones disposed on the outer surface of the support structure, at least one air impermeable fence zone adjacent to each vacuum zone, and at least one air permeable fence zone adjacent to each vacuum zone. The air permeable fence zone may comprise an ambient air entry conduit in fluid communication with an ambient air exit port. A vacuum applied beneath the vacuum zones may draw ambient air into the ambient air entry conduit and radially outward from the ambient air exit port. In some embodiments, the support structure may be a laydown drum.

In some embodiments, the ambient air entry conduit does not extend through the surface of the laydown drum. A collective surface area of vacuum zones, air permeable fence zones, and air impermeable fence zones may equal a surface area of the outer surface of the laydown drum. The ambient air entry conduits may comprise fins at one or more laterally outermost edges of the ambient air entry conduits, whereby the fins direct ambient air into the ambient air entry conduit when the laydown drum is rotated. The vacuum zones may comprise a screen having a plurality of apertures.

The air impermeable fence zones and the air permeable fence zones may have a greater height relative to the outer surface of the support structure than the vacuum zones. The air impermeable fence zones and the air permeable fence zones may be less than about 7 mm higher than the vacuum zones relative to the outer surface of the support structure.

In some embodiments, the disclosure relates to a method of forming a batt comprising particulate material, the method comprising the steps of providing a support structure, the support structure having an outer surface and a plurality of vacuum zones, the vacuum zones being substantially permeable to permit vacuum air to pass through and into the laydown drum, a plurality of air impermeable fence zones, the air impermeable fence zones being substantially impermeable to inhibit air to pass through, the air impermeable fence zones being positioned laterally adjacent the vacuum zones on the outer surface of the support structure, and a plurality of air permeable fence zones, the air permeable fence zones comprising an ambient air entry conduit in communication with an ambient air exit port, the air permeable fence zones being substantially permeable to permit ambient air to pass through the air permeable fence zones, the air permeable fence zones being positioned between the vacuum zones on the surface of the support structure, generating a vacuum through the laydown drum such that air is drawn through the vacuum zones and the air permeable fence zones, and depositing a dispersion comprising air and particulate material such that the vacuum applied to the vacuum zones directs the dispersion to the vacuum zones whereupon the particulate material is positioned to form a batt.

The method may further comprise providing a web of substrate material, pulling the web of substrate material substantially adjacent to the vacuum zones, and depositing the dispersion of air and particulate material on the web in the vacuum zones. In some embodiments, the method may include severing the first web to form a plurality of discrete batts. The method may further comprise the steps of providing a second web of material, positioning the second web of material adjacent the particulate material, and combining the second web of material to the first web of material. The combined webs may be severed to form a plurality of discrete batts.

The first and second webs may be combined prior to severing the web to form the plurality of batts. The particulate material may comprise superabsorbent polymer particles. The superabsorbent polymer particles may be shielded after they are deposited. The first and second web of materials may be bonded.

BRIEF DESCRIPTION OF THE DRAWINGS

FIG. 4E shows exemplary vacuum and fence zones.

DETAILED DESCRIPTION OF THE EMBODIMENTS

Figure 1B:
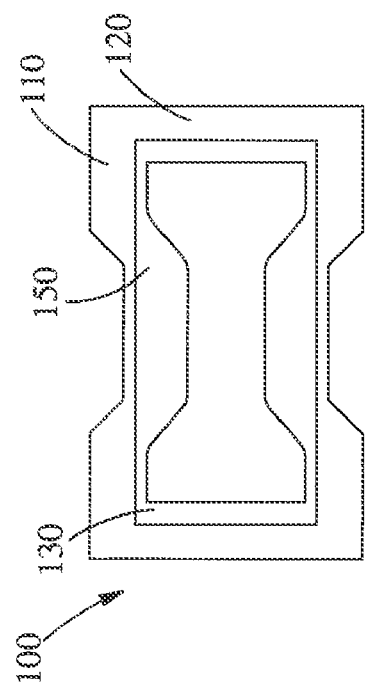
FIG. 1B shows an exemplary absorbent article.

The following term explanations may be useful in understanding the present disclosure.

The term "absorbent article" herein refers to devices which absorb and contain body exudates and, more specifically, refers to devices which are placed against or in proximity to the body of the wearer to absorb and contain the various exudates discharged from the body, such as: incontinence briefs, incontinence undergarments, absorbent inserts, diaper holders and liners, feminine hygiene garments and the like. The absorbent article may have an absorbent core having a garment-facing surface and a body-facing surface when fitted to a wearer, a liquid permeable topsheet positioned adjacent the body-facing surface of the absorbent core, and a liquid impermeable backsheet positioned adjacent the garment-facing surface of the absorbent core.

The term "air permeable" is used herein to describe a surface which presents little or no resistance to air flow through the surface. Examples include screens, meshes, holes, and open areas. A surface which is air permeable in itself may present increased resistance to air flow as materials, such as nonwoven webs, fibers, or particulates, are deposited on the surface. Air permeable screens may be perforated materials defined by their thickness, hole size, and open area. Exemplary screens may have a thickness from about 0.125 mm to about 0.5 mm, for example 0.254 mm, with hole diameters from about 0.254 mm to about 3 mm, for example 1.0 mm, and open areas from about 30% to about 70%. Said air permeable screens may have Darcy Porosity values from about 0.30 to about 0.70 where porosity $n=V_v/V_t$ and $V_v$=Void Volume and $V_t$=Total Volume. Air permeable screens may also be defined by Darcy Void Ratio such screens having a void ratio from about 0.43 to about 2.3, for example having a void ratio of 0.75, where the void ratio $e=V_v/V_s$ and $V_v$=Void Volume and $V_s$=Solid Volume. Air permeable surfaces that are wire screens may be defined by wire diameter, width of opening between wires, and open area. Such wire screens may have wire diameters from about 0.114 mm to about 1.19 mm, for example 0.457 mm in diameter; they may have opening widths between wires from about 0.14 mm to about 3.05 mm, for example 1.13 mm; they may have overall open areas from about 30.3% to about 51.8%, for example 50.7%. Screen Mesh may also be used to define the air permeability of the surface and may range for 6 Mesh to 100 Mesh most preferably 16 Mesh, where Mesh=1/(D+O) and D=Wire Diameter and O=Opening between wires.

The term "air impermeable" is used herein to describe a surface which presents significant resistance to air flow through the surface, effectively allowing zero air flow through the surface when subjected to a negative pressure equal to or less than minus 0.122 atmospheres or negative 50 inches of water.

The term "disposable" is used herein to describe absorbent articles which generally are not intended to be laundered or otherwise restored or reused as absorbent articles (i.e., they are intended to be discarded after a single use and, preferably, to be recycled, composted or otherwise discarded in an environmentally compatible manner).

The term "diaper" herein refers to an absorbent article generally worn by infants and incontinent persons about the lower torso to receive and contain excreta.

The term "longitudinal" herein refers to a direction running parallel to the maximum linear dimension of the article and includes directions within ±45° of the longitudinal direction.

The term "lateral" herein refers to a direction which is perpendicular to the longitudinal direction.

The term "fluff material" refers to any material suitable for suspending and/or entangling with superabsorbent polymer. Fluff material may be made of a variety of materials including, but not limited to, synthetic fibers having a length suitable for airlaying, cellulose fibers including cross-linked cellulose fibers, or the like, and combinations thereof.

The term "substantially adjacent" herein refers to two or more items positioned so that they are lying near or close to one another, or so that they are touching at one side or surface. Substantially adjacent items may be adjacent over only a portion of their side or surface. For example, placing a continuous web material substantially adjacent to a drum may involve adjacency between only a portion of the continuous web material and a portion of the drum's surface.

The term "superabsorbent polymer" herein refers to a polymer which is capable of absorbing within the polymer at least 10 times its weight in deionized water. Superabsorbent polymer may be made of a variety of materials including, but not limited to, polyacrylic acid, sodium polyacrylate, polyacrylamide, polyacrylonitrile, polyvinyl alcohol, maleic anhydride, a polyether, a condensed polymer, a polysaccharide such as starch or cellulose, a protein such as collagen, or the like, and combinations thereof. Examples of the superabsorbent polymers include: a cross-linked compound of sodium polyacrylate, a graft copolymer of starch having sodium polyacrylate, or a graft copolymer of cellulose having polyacrylonitrile chains.

The present disclosure relates to apparatuses and methods for manufacturing absorbent core assemblies for disposable absorbent products, and in particular, for forming batts comprising particulate material used in absorbent core assemblies. In particular, the methods and apparatuses herein are configured to channel air through a conduit to help direct the particulate material to desired locations during manufacture.

For example, some embodiments include a rotating laydown drum having an outer surface with defined vacuum zones and fence zones. In one embodiment, a vacuum system in fluid communication with the laydown drum may draw air from outside the laydown drum through the vacuum zones and into the laydown drum. As discussed in more detail below, the vacuum applied to the vacuum zones may also be used to draw air through a conduit on the surface of the laydown drum and through the air permeable fence zones. During the manufacture of absorbent core assemblies, particulate material is deposited onto a web of material while the web is substantially adjacent to the outer surface of the laydown drum. As the particulate material is deposited onto the web, air traveling through the vacuum zones into the laydown drum helps direct, place, and hold the particulate material in desired positions on the web. At the same time, air pulled through the air permeable fence zones moves generally away from the laydown drum as it first exits the air permeable fence zones, and helps prevent particulate material from being deposited on the web outside of desired locations.

The present disclosure further relates to the formation of a batt comprising particulate material without the immediate use of a web material. A laydown drum having vacuum zones and air permeable fence zones as described above can be used to form a batt comprising particulate material on a mesh or screen disposed in the vacuum zone. The batt can then be transferred to a supporting material, such as a web or a partially formed absorbent article. Throughout this description, a laydown drum is referenced as the subjacent support for the vacuum zones, air permeable fences, and air impermeable fences. However, a variety of subjacent support structures would be acceptable. For example, it would be possible to adapt the embodiments of the disclosure to use, instead of a laydown drum, a conveyor belt, another moving surface, or even to configure a fixed support structure.

The following provides a description of a basic diaper construction with reference to accompanying figures to help illustrate the apparatuses and methods described below. As such, it is to be appreciated that other diaper constructions can be utilized with the methods and apparatuses herein. Although the present disclosure is provided in the context of manufacturing diapers, it is to be appreciated that the apparatuses and methods herein may be applied to the manufacture of various types of absorbent articles.

Figure 1A:
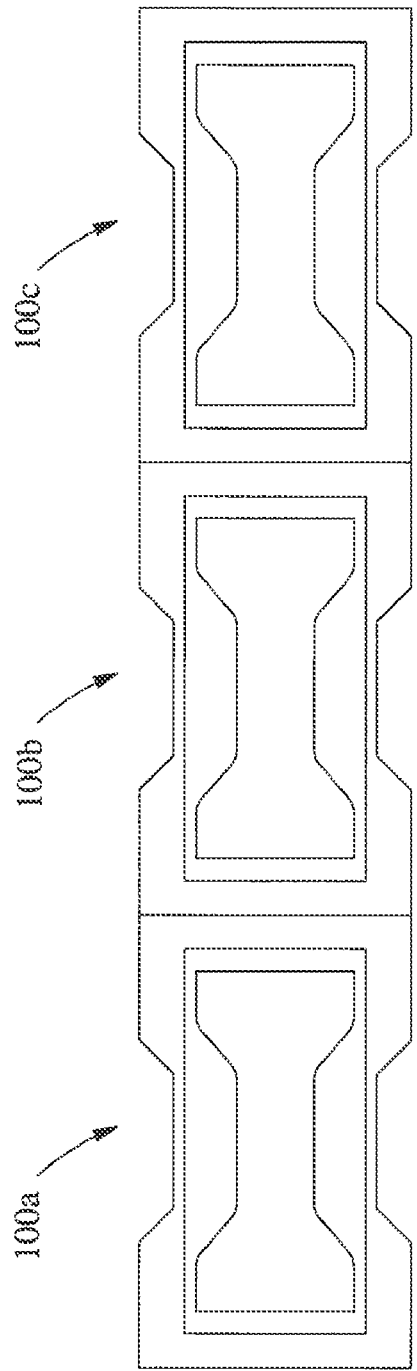
FIG. 1A shows a series of absorbent articles made from a plurality of web materials.
Figure 2A:
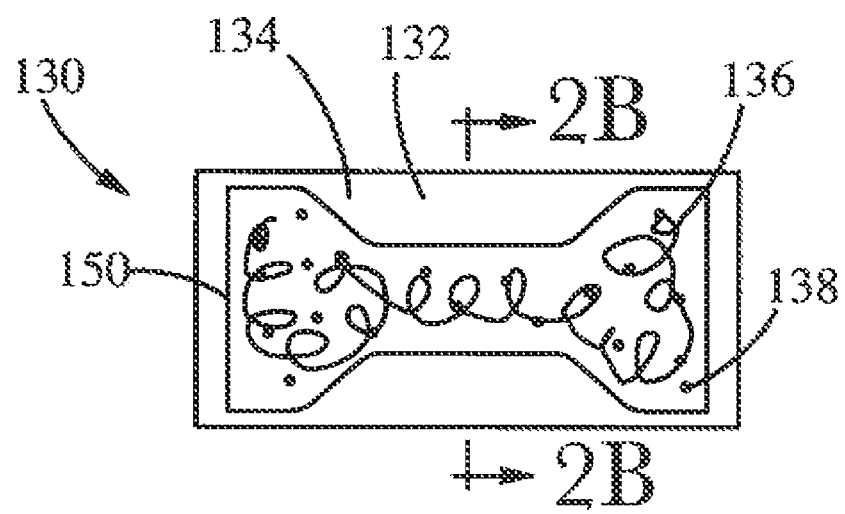
FIG. 2A shows the absorbent core assembly from FIG. 1A.
Figure 2B:
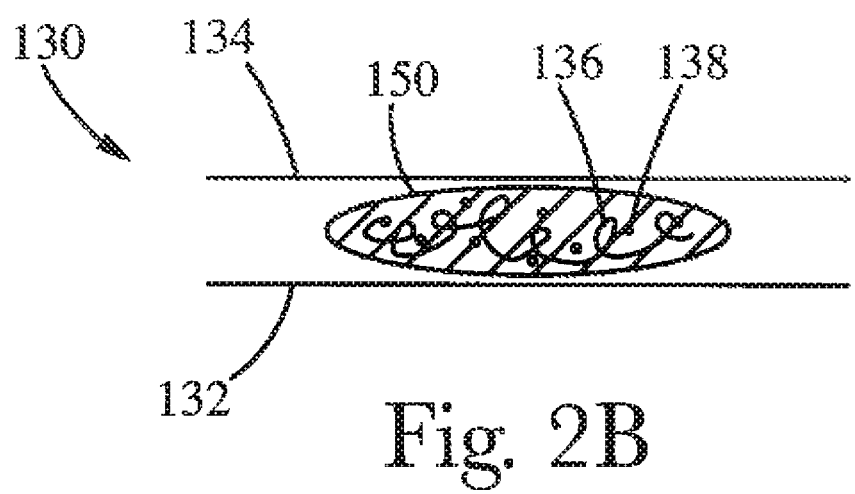
FIG. 2B shows a cross-sectional view of the absorbent core assembly from FIG. 2A taken along line 2B-2B.

During the manufacture of absorbent articles, substrates may be combined with the other substrates and/or discrete components to create a continuous length of absorbent articles. At a downstream portion of the manufacturing process, the continuous length of absorbent articles is subjected to a final knife cut to create separate and discrete absorbent articles. FIG. 1A shows a portion of a continuous length of absorbent articles made from a combination of web and component materials. In particular, FIG. 1A shows a first absorbent article 100a, a second absorbent article 100b and a third absorbent article 100c in an end-to-end configuration, as might exist prior to a final knife cut within a manufacturing process. FIG. 1B shows a discrete absorbent article in the form of a diaper. The absorbent article 100 includes a topsheet 110, a backsheet 120 and an absorbent core assembly 130 containing a batt 150 of particulate material. The absorbent core assembly 130 of FIG. 1B is shown in detail in FIGS. 2A and 2B. Absorbent core assembly 130 may comprise dusting layer 132, core wrap layer 134, and a mixture of fibrous and particulate material, for example fluff material 136 and superabsorbent polymer (hereinafter SAP) 138, positioned between dusting layer 132 and core wrap layer 134 and forming batt 150. As shown in FIG. 2B, dusting layer 132 may be positioned on one side of batt 150 and core wrap layer 134 may be positioned opposite dusting layer 132; however, a variety of other configurations are possible.

Figure 3:
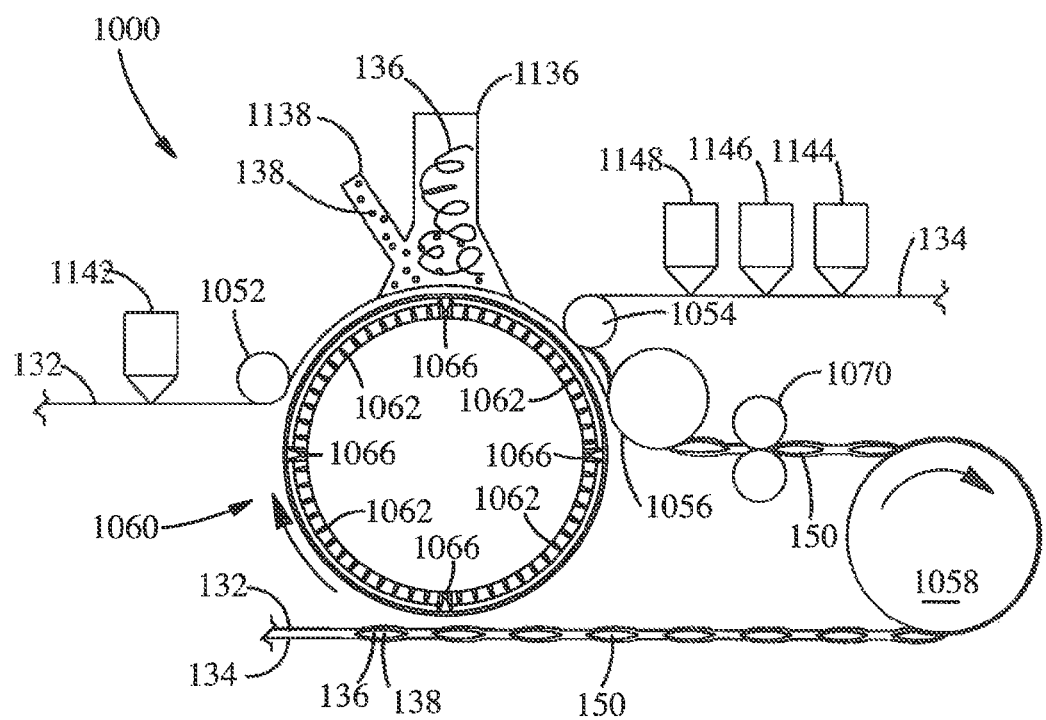
FIG. 3 shows a schematic representation of an exemplary manufacturing process for forming absorbent core assemblies.

Absorbent core assemblies, and in particular, batts, may be formed by depositing material, including particulate material, onto a web or substrate advancing along a rotating laydown drum. FIG. 3 shows an exemplary manufacturing process 1000 for forming a batt wherein material including particulate material is deposited onto a continuous web of dusting layer material 132 advancing through the process. Process 1000 may utilize various mechanisms and a variety of other web handling devices, such as laydown drum 1060, SAP applicator 1138, or fluff material deposition chute 1136. Central adhesive applicator 1142 may apply adhesive to at least one side of the dusting layer. While a variety of adhesive application patterns may be used, one such pattern is depicted later in FIG. 6A. After the central adhesive is applied, dusting layer 132 may be fed to an underneath position in relationship to fluff material deposition chute 1136. Throughout this manufacturing process, a variety of web handling devices may be used including, but not limited to, idler rollers 1052, 1054, 1056, 1058. Next, batt 150 may be formed by SAP 138 and fluff material 136 being applied to the top of dusting layer 132 with the aid of air being drawn by vacuum through and into the interior of laydown drum 1060. As discussed in more detail below, laydown drum 1060 may include multiple zones to help deposit and maintain the SAP and fluff material in desired locations on the dusting layer, such as vacuum zones 1062, air impermeable fence zones 1064 and air permeable fence zones 1066.

It is also possible to form batt 150 using process 1000 without dusting layer 132. In such an embodiment, the substrate may be part of laydown drum 1060. For example, the substrate may be a screen disposed in vacuum zones 1062 to hold SAP 138 and fluff material 136. In some configurations, the screen is made of metal for durability, but it may be made of any suitable material which will permit air to pass through the screen under the influence of a vacuum and will retain SAP 138 and fluff material 136 to foam batt 150. In some embodiments, the metal screen may have a plurality of small apertures, each having a diameter of approximately 0.011 inches (approximately 0.028 cm). It will be appreciated that the shape, configuration, material, and size of the screen and the apertures may be adjusted depending upon the specific set-up of process 1000, including the magnitude of the vacuum used, the size and quantity of particles distributed to each batt 150, and the desired shape and thickness of batt 150. Once formed, batt 150 may then be transferred from the screen on the surface of laydown drum 1060 to any desired carrier, such as dusting layer 132 or an alternate substrate.

In parallel with the processes described above, a web of core wrap material 134 may also be fed into the process in a direction relatively towards the fluff material deposition chute 1136. Adhesive may be applied to the core wrap, for example, by side adhesive applicator 1144, end adhesive applicator 1146, and auxiliary adhesive applicator 1148. While a variety of adhesive application patterns may be used, one such collection of patterns is depicted in FIG. 6C and discussed below. After the adhesive is applied, the core wrap material may be brought into contact with dusting layer 132 and batt 150 formed by the mixture of SAP 138 and fluff material 136. Next, the webs of materials may be bonded. For example, phased bonding roll 1070 may be used to provide intermittent bonding so as to bond the layers of materials between discrete batts 150 formed by the depositions of SAP and fluff material.

Figure 4A:
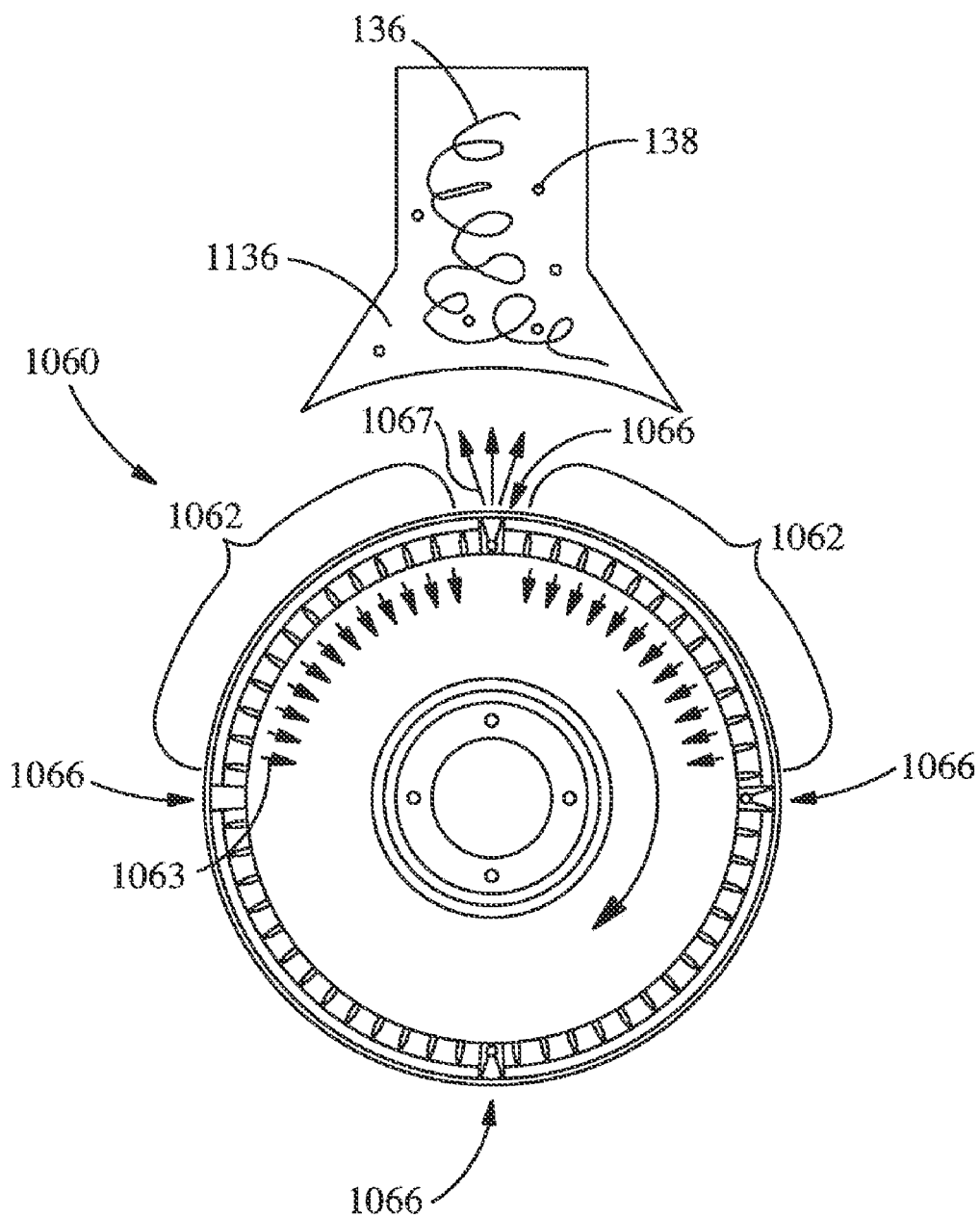
FIG. 4A shows a cross-sectional view of a laydown drum.
Figure 4B:
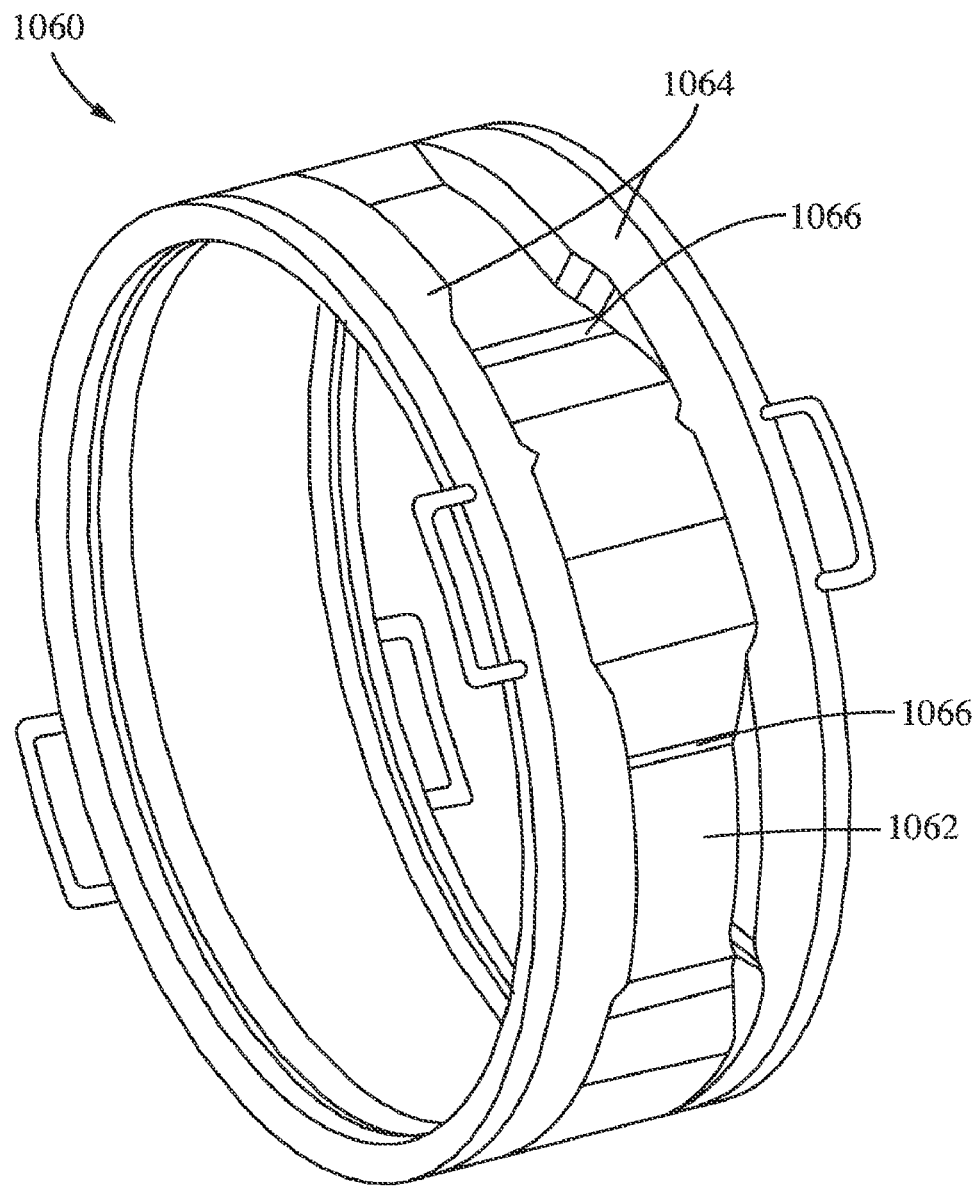
FIG. 4B is an isometric view of a laydown drum.

As mentioned above, the laydown drum includes vacuum and fence zones configured to maintain the particulate material deposited on the web in desired locations. As shown in FIGS. 4A and 4B, the surface of laydown drum 1060 may include at least two distinct zones, namely, a plurality of vacuum zones 1062 and a plurality of air permeable fence zones 1066. Also shown in FIG. 4A is fluff material deposition chute 1136 wherein SAP 138 and fluff material 136 are dispersed and mixed in air to form an air/particulate dispersion. It is from fluff material deposition chute 1136 that SAP 138 and fluff material 136 are deposited to form the batts 150. By way of pulling air 1063 through vacuum zones 1062, the air/particulate dispersion is directed to the vacuum zones whereupon SAP 138 and fluff material 136 are positioned to form discrete batts 150 of absorbent core material. With the additional use of ambient air flow 1067 through air permeable fence zones 1066, the formation of discrete batts is improved such that the amount of loose particles of SAP 138 and/or fluff 136 material inadvertently positioned within the space between the batts is minimized.

Figure 4C:
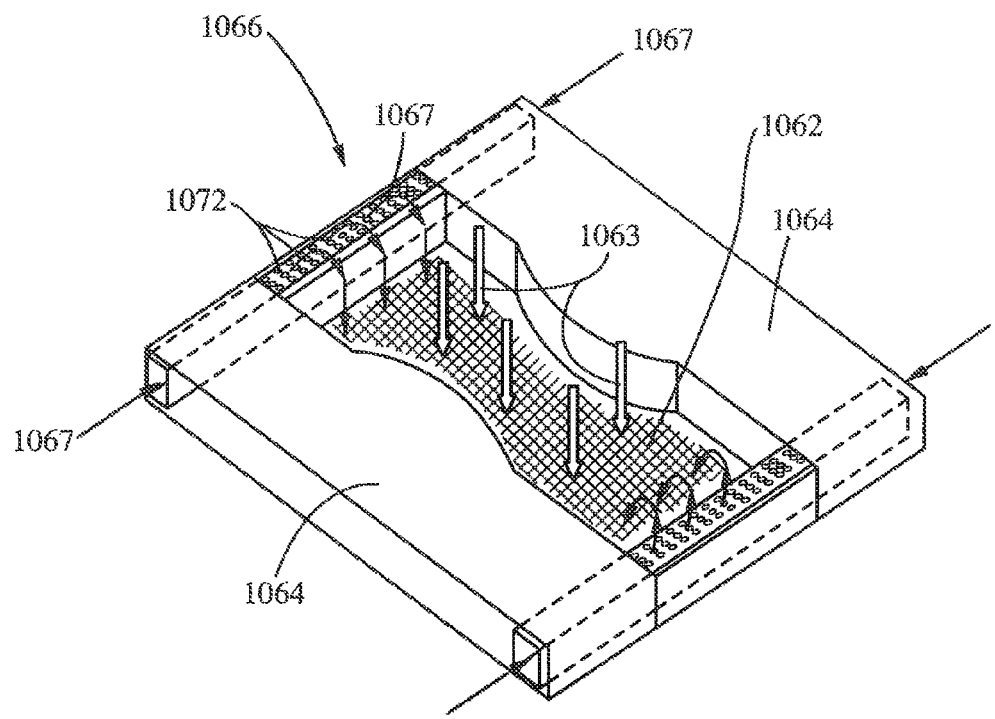
FIG. 4C shows a detailed perspective view of vacuum and fence zones on the laydown drum of FIG. 4A.

As shown in FIG. 4C, an air permeable fence zone 1066 may be located at each longitudinal end of vacuum zone 1062. Air flow through the vacuum zone 1063 is driven by a vacuum fan or pump (not shown), which pulls air into the laydown drum. Air flow through the air permeable fence zones 1067 is drawn by the vacuum applied to the vacuum zones, and extends generally perpendicular to the laydown drum (not shown) at the surface of the laydown drum, over the air permeable fence, and eventually through the vacuum zone into the laydown drum. The air flow through the air permeable fence zones 1067 begins at the ambient air entry conduit 1070, and continues out the ambient air exit ports 1072. An individual vacuum zone 1062 may also be laterally adjacent to air impermeable fence zones 1064.

Figure 4D:
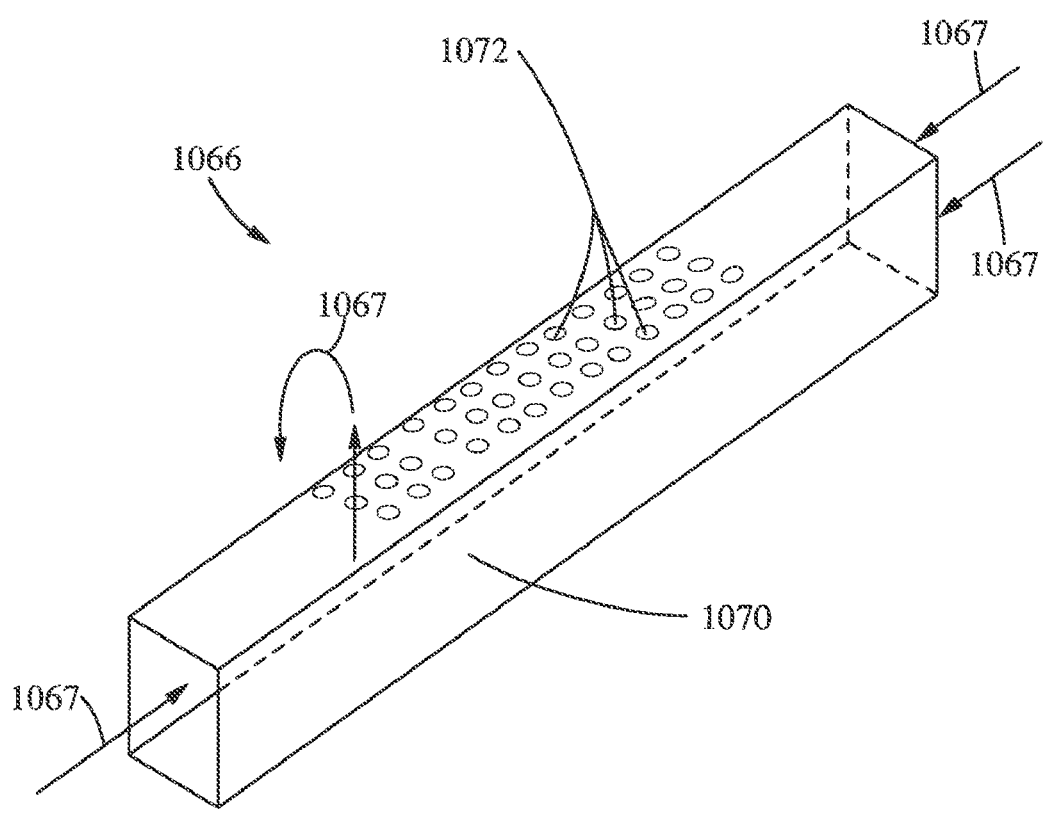
FIG. 4D shows a detailed perspective view of an air permeable fence zone from FIG. 4C.
Figure 4F:
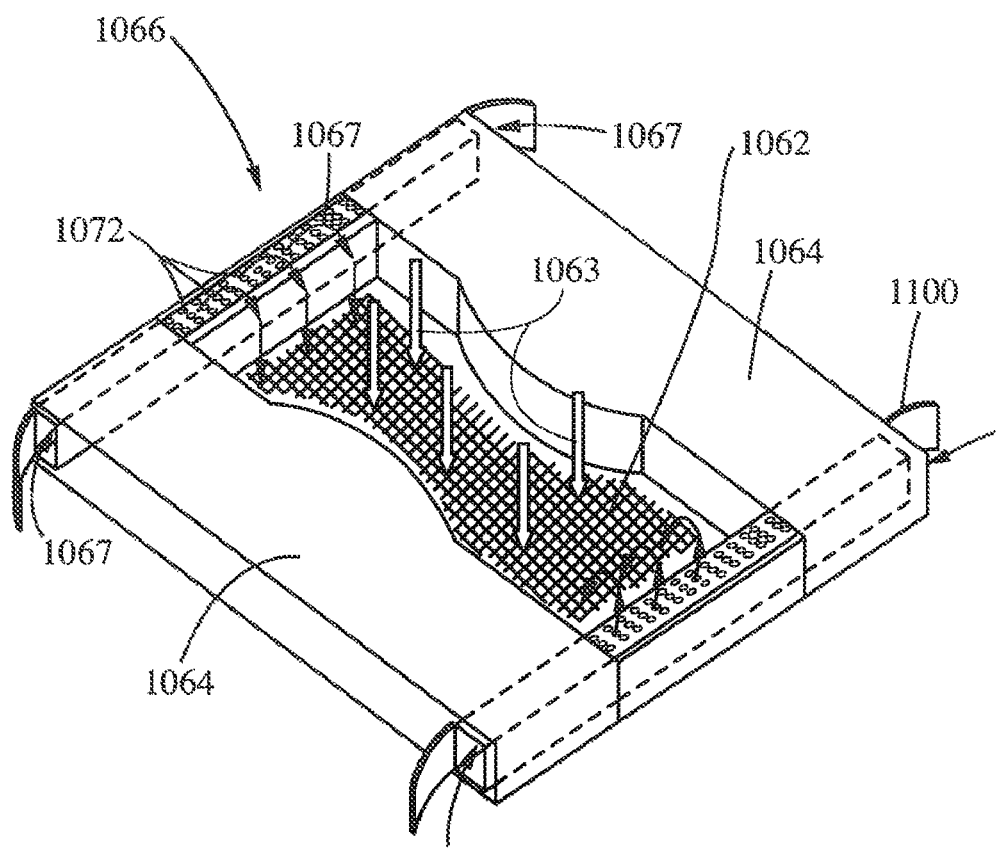
FIG. 4F shows air permeable fence zones having fins.

As shown in FIG. 4D, ambient air is drawn into the ambient air entry conduit 1070 of air permeable fence zone 1066 and flows through ambient air exit ports 1072. Unlike vacuum zone 1062, through which air flows into laydown drum 1060, the ambient air entry conduit 1070 may be disposed on the surface of the laydown drum. That is, the air permeable fence zones may be configured such that air entry conduit 1070 do not extend below the surface of laydown drum 1060. The embodiment depicted in FIG. 4D shows an air permeable fence zone 1066 having a square cross-section, air entry conduit 1070, and a plurality of air exit ports 1072. The air permeable fence zone 1066 may have any of a multitude of alternate cross-sectional shapes, such as triangles, circles, ovals, parallelograms, etc., and the cross-sectional shape or size may vary over the length of the air permeable fence zone 1066. The air permeable fence zone 1066 may also have one air entry conduit 1070 or a plurality of air entry conduits 1070, and one or several distinct air exit ports 1072. The sides and bottom of air entry conduits 1070 may be air impermeable to facilitate air flow through air exit ports 1072. The amount, force, and direction of the air flow through the air permeable fence zones 1066 can be modified by varying the configurations of air entry conduits 1070 and air exit ports 1072. In some embodiments, the ends of air exit ports 1072 may include fins 1100, as shown in FIG. 4F, such that ambient air is directed through air permeable fence zones 1066 by the rotation of laydown drum 1060.

Vacuum zone 1062 is recessed relative to air impermeable fence zones 1064, as shown in FIG. 4E. The height of air impermeable fence zones 1064 relative to vacuum zone 1062 may vary depending upon the desired thickness of batt 150, and the particulars of manufacturing process 1000. If a web is used as a substrate moving over the surface of laydown drum 1060 to receive batt 150, the height of air impermeable fence zones 1064 may be limited by the minimum acceptable edge definition of batt 150. In some instances, the vacuum applied to vacuum zones 1062 may pull the web closely against the edges of vacuum zone 1062 and the fence zones, allowing SAP 138 and fluff material 136 to form distinct, even edges having the shape of the vacuum zone. If the height of air impermeable fence zones 1064 is too great, the web may not conform to the edges of vacuum zone 1062, and SAP 138 and fluff material 136 may not be distributed evenly where the web is bowed. Thus, if the height of air impermeable fence zones 1064 is too great, batts 150 may have indistinct, uneven edges which are functionally or aesthetically unacceptable. In some configurations, the maximum air impermeable fence height suitable for use with a web or other substrate is approximately 5-7 mm. The height of air permeable fence zones 1066 may also be limited by similar concerns, although it is not necessary that the height of air permeable fence zones 1066 match each other or the height of air impermeable fence zones 1064.

Figure 5:
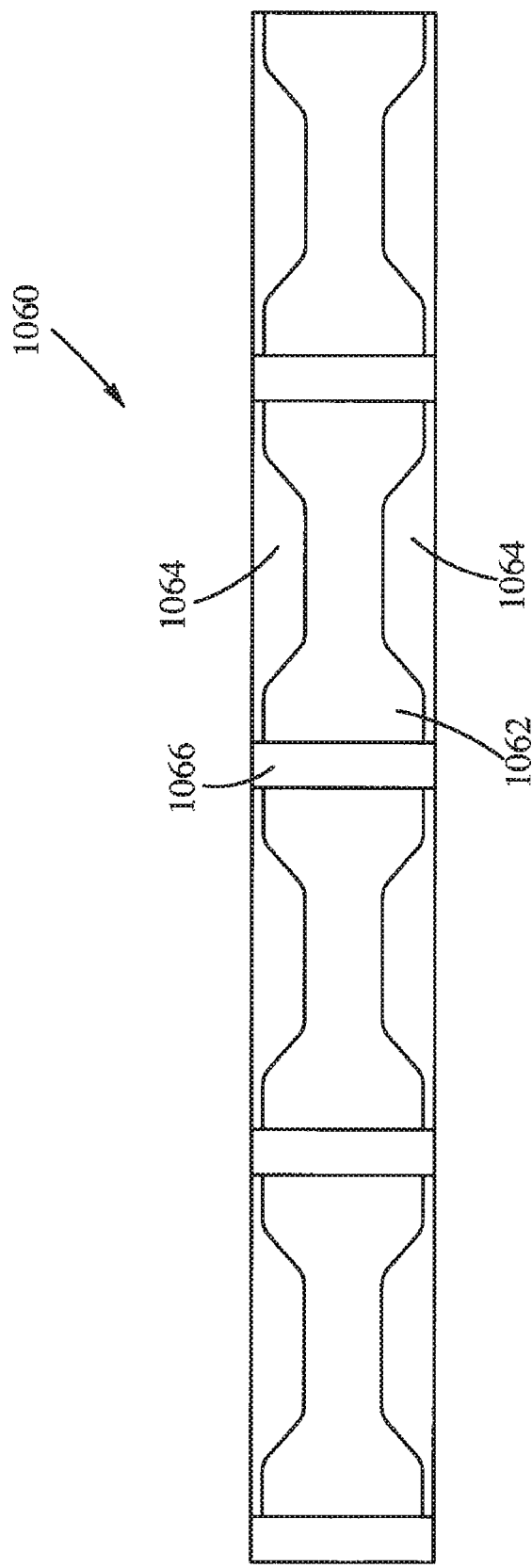
FIG. 5 shows a laid-out view of the surface of laydown drum from FIG. 4B.

FIG. 5 shows a laid-out view of the surface of laydown drum 1060 from FIG. 4. In the embodiment shown, vacuum zones 1062 have an hourglass shape, however, vacuum zones 1062 can have nearly any shape to form the desired outline of discrete batts 150. Vacuum zones 1062 are substantially air-permeable to allow air to pass through. In contrast, air impermeable fence zones 1064 may be used to inhibit air flow and thus inhibit the placement of SAP/fluff material in the locations of air impermeable fence zones 1064. Air impermeable fence zones 1064 need not be completely air impermeable, so long as they are sufficiently air impermeable to inhibit air to pass through under vacuum. In some embodiments, the air impermeable fence zones may be laterally adjacent to the vacuum zones as shown in FIG. 5.

The air flow generated by the vacuum under the vacuum zones pulls air through air permeable fence zones 1066. Air flow 1067 through air permeable fence zones 1066 may, at least initially, be generally away from the surface of laydown drum 1060, or radially outward from the surface of the laydown drum, as shown in FIGS. 4C and 4D. Thus, air flow 1067 through air permeable fence zones 1066 limits the placement of SAP/fluff material in these locations by blowing away any SAP/fluff material inadvertently deposited in the vicinity of air permeable fence zones 1066. The use of air permeable fence zones 1066 in the area between the vacuum zones helps reduce the amount of deposited SAP/fluff material which would ultimately be positioned within the waist region of the resulting absorbent article. Having SAP positioned in the waist region may be undesirable, for example, because the SAP particles are not constrained by fluff material or the core cover of the absorbent core, thus the SAP particles may have a greater tendency to migrate through the top sheet and come in contact with the wearer. Particulate deposits in the waist region of the absorbent article may also interfere with bonding, such as adhesive bonding or mechanical bonding, in that region. The use of ambient air in air permeable fence zones 1066 means that no additional equipment or power input is necessary to produce forced air to blow SAP particles away from the spaces between the batts.

Figure 6A:
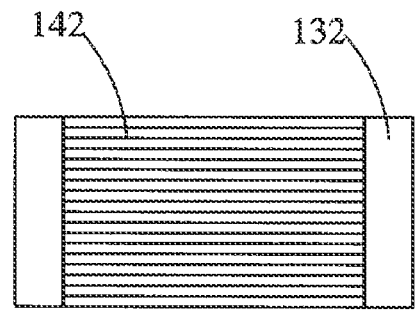
FIG. 6A shows a dusting layer having a central adhesive applied in a striped pattern.
Figure 6B:
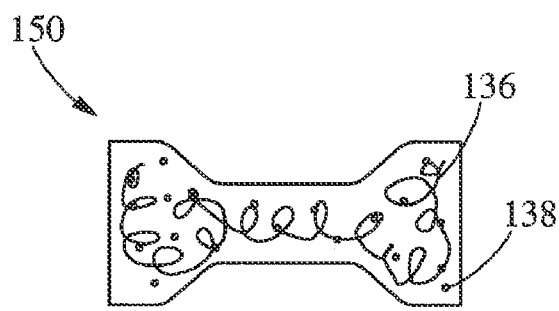
FIG. 6B shows a vacuum-formed outline of a mixture of fluff material and SAP.
Figure 6C:
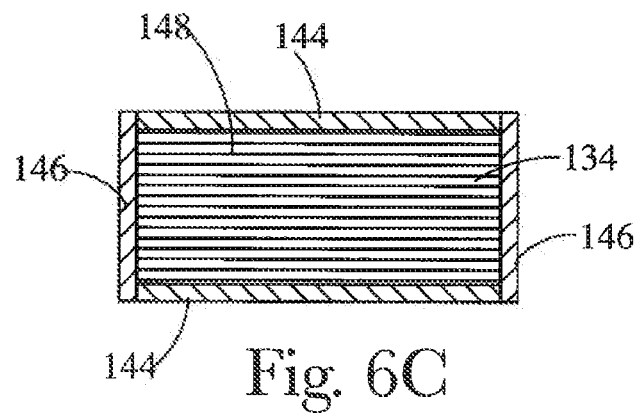
FIG. 6C shows an underlying layer of core wrap material with a plurality of adhesive application patterns.

FIG. 6A shows dusting layer 132 having central adhesive 142 applied in a striped pattern. FIG. 6B shows the vacuum-formed outline of batt 150 containing a mixture of fluff material 136 and SAP 138. While an hour-glass shape is shown, other shapes may be used. FIG. 6C shows an underlying layer of core wrap material 134 with a plurality of adhesive application patterns, namely, side adhesive 144 and end adhesive 146 applied to the perimeter of the core wrap. Additionally, auxiliary adhesive 148 may be applied in the field within the side and end adhesives. The use of adhesives helps to form a laminate of the dusting layer, the batt containing fluff material/SAP, and the core wrap. While a striped pattern is shown in FIGS. 6A and 6C, various other adhesive application patterns may be used.

Figure 7:
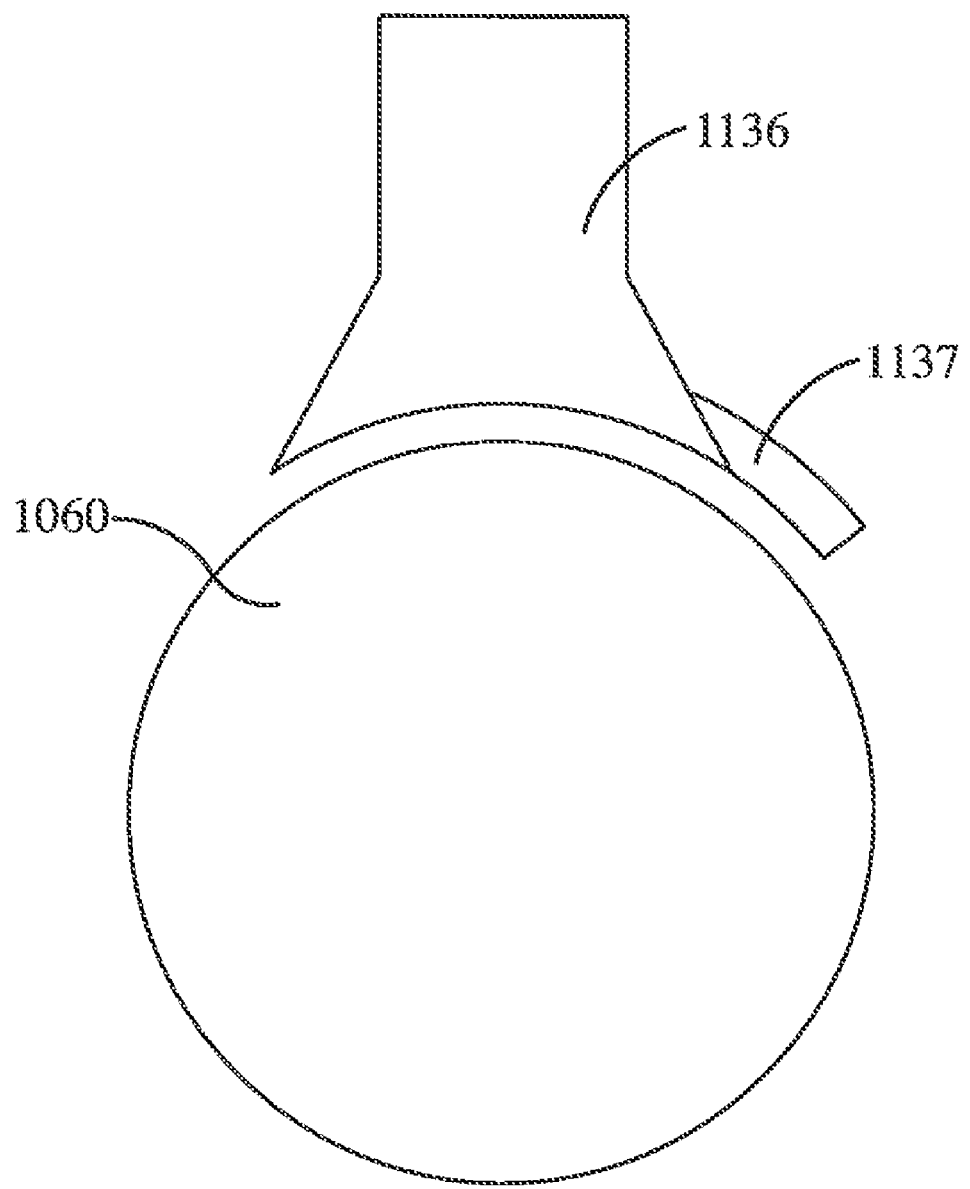
FIG. 7 shows an SAP shield adjacent the fluff material deposition chute of FIG. 3.

FIG. 7 shows the addition of SAP shield 1137 which may be attached to fluff material deposition chute 1136 so as to extend the amount of coverage around the laydown drum 1060 and thus help minimize the amount of SAP particles which might otherwise bounce off of the laydown drum and away from the web. While particulate material comprising SAP and fluff material was discussed above, it is also possible to use only SAP, or substantially only SAP, or substantially only fluff material. For example, the particulate material may include greater than 90% SAP, or greater than 95% SAP, or even greater than 98% SAP. The particulate material may also comprise adhesive. The adhesive may be mixed with the particulate material prior to deposition, or the adhesive may be applied before, during, or after the deposition of the particulate material.

Various known processes for producing absorbent core particulate batts could be modified to include the air permeable fence zones disclosed herein. For example, air permeable fence zones could be incorporated into the processes described in U.S. Patent Application No. 61/091,799 by Hundorf, et al., filed Aug. 26, 2008; and in International Patent Application Publication No. WO 2008/117109 A1 by Bianco, et al., filed Dec. 3, 2007; or in virtually any other core forming process.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for distributing particulate material, the method comprising the steps of:
    providing an air permeable deposition surface bounded on at least one side by an air permable non-deposition surface, the air permeable non-deposition surface being in fluid communication with ambient air; and
    causing airflow through the air permeable deposition surface as a particulate material is deposited on the air permeable deposition surface;
    wherein the airflow through the air permeable deposition surface causes ambient air to flow through the air permeable non-deposition surface and toward the air permeable deposition surface, whereby the airflow directs the particulate material away from the air permeable non-deposition surface and toward the air permeable deposition surface.

2. The method of claim 1, wherein no positive pressure is applied to the air permeable non-deposition surface.

3. The method of claim 1, wherein the particulate material is deposited from a deposition chute.

4. The method of claim 3, wherein the deposition chute comprises a shield.

5. The method of claim 1, wherein the particulate material is mixed with fluff material.

6. The method of claim 5, wherein the particulate material comprises greater than 90% of a superabsorbent polymer.

7. The method of claim 6, wherein the particulate material comprises greater than 95% of a superabsorbent polymer.

8. The method of claim 7, wherein the particulate material comprises greater than 80% of a superabsorbent polymer.

9. The method of claim 1, further comprising mixing the particulate material with an adhesive.

10. The method of claim 9, wherein the particulate material is mixed with an adhesive prior to depositing the particulate material on the air permeable deposition surface.

11. The method of claim 1, further comprising forming a batt from the particulate material on the air permeable deposition surface.

12. The method of claim 11, further comprising transferring the batt to a web.

13. The method of claim 12, further comprising assembling the web comprising the batt into an absorbent article.

14. The method of claim 13, wherein the absorbent article is a diaper.

15. An apparatus for distributing particulate material, the apparatus comprising:
    an air permeable deposition surface bounded on at least one side by an air permeable non-deposition surface, the air permeable non-deposition surface comprising an ambient air entry conduit and an ambient air exit port;
    a vacuum source in fluid communication with the air permeable deposition surface; and
    a particulate material deposition chute overlying the air permeable deposition surface;
    wherein a vacuum applied to the air permeable deposition surface creates air flow beginning at the ambient air entry conduit and continuing out the ambient air exit port, such that air flows away from the air permeable non-deposition surface and into the air permeable deposition surface without the application of positive pressure to the air permeable non-deposition surface.

16. The apparatus of claim 15, wherein the particulate material deposition chute comprises a shield.

17. The apparatus of claim 15, wherein the ambient air exit port is substantially orthogonal to the ambient air entry conduit.

18. The apparatus of claim 15, further comprising an air impermeable non-deposition surface bounding the air permeable deposition surface on at least one side of the air permeable deposition surface.

19. The apparatus of claim 18, comprising at least two air permeable non-deposition surfaces, and at least two air impermeable non-deposition surfaces.

20. The apparatus of claim 15, wherein the deposition and non-deposition surfaces are disposed on a laydown drum.

* * * * *